(12) United States Patent
Sung et al.

(10) Patent No.: US 9,452,130 B2
(45) Date of Patent: *Sep. 27, 2016

(54) PHARMACEUTICAL COMPOSITION FOR PREPARING DRUG DELIVERY NANO/MICRO BUBBLES

(71) Applicant: National Tsing Hua University, Hsinchu (TW)

(72) Inventors: Hsing-Wen Sung, Hsinchu (TW); Er-Yuan Chuang, Hsinchu (TW); Po-Yen Lin, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 38 days.

This patent is subject to a terminal disclaimer.

(21) Appl. No.: 14/556,740

(22) Filed: Dec. 1, 2014

(65) Prior Publication Data

US 2016/0015629 A1    Jan. 21, 2016

(30) Foreign Application Priority Data

Jul. 18, 2014 (TW) .............................. 103124722 A

(51) Int. Cl.
| | | |
|---|---|---|
| *A61K 47/26* | (2006.01) | |
| *A61K 9/14* | (2006.01) | |
| *A61K 38/28* | (2006.01) | |
| *A61K 9/46* | (2006.01) | |
| *A61K 9/51* | (2006.01) | |
| *A61K 9/127* | (2006.01) | |
| *A61K 47/02* | (2006.01) | |
| *A61K 47/20* | (2006.01) | |

(52) U.S. Cl.
CPC ........... *A61K 9/0007* (2013.01); *A61K 9/1271* (2013.01); *A61K 9/14* (2013.01); *A61K 9/5123* (2013.01); *A61K 9/5169* (2013.01); *A61K 38/28* (2013.01); *A61K 47/02* (2013.01); *A61K 47/20* (2013.01); *A61K 47/26* (2013.01)

(58) Field of Classification Search
CPC ......... A61K 47/26; A61K 9/14; A61K 38/28
See application file for complete search history.

(56) References Cited

U.S. PATENT DOCUMENTS

| | | | |
|---|---|---|---|
| 7,358,226 B2 * | 4/2008 | Dayton ................ | A61B 8/4483 424/130.1 |
| 2010/0158813 A1 * | 6/2010 | Paradossi ............... | A61K 9/122 424/9.52 |
| 2013/0129635 A1 * | 5/2013 | Nagy ................... | A61K 49/223 424/9.52 |

OTHER PUBLICATIONS

Prajapati, J. et al. "Synthesis, characterization and application of microbubbles: A Review", Int'l J Pharm. Sci. Res. (2012), vol. 3, Iss. 06, pp. 1532-1543.*

* cited by examiner

*Primary Examiner* — Gina Justice
(74) *Attorney, Agent, or Firm* — Muncy, Geissler, Olds & Lowe, P.C.

(57) ABSTRACT

The pharmaceutical composition includes a drug layer comprising an active ingredient, a surfactant, an acidic component and an effervescent ingredient. The active ingredient comprises a nucleic acid, a peptide or a protein. The acidic component and effervescent ingredient of the drug layer are dissolved in the water to react for generating carbon dioxide and bubbles thereof. The surfactants surround the carbon dioxide gas core and form a double-layer structure having an inner layer and outer layer. The active ingredient is embedded in a gap formed between the inner layer and the outer layer of the double-layer structure.

14 Claims, 6 Drawing Sheets

PHARMACEUTICAL COMPOSITION FOR PREPARING DRUG DELIVERY NANO/MICRO BUBBLES

BACKGROUND OF THE INVENTION

1. Field of the Invention

The present invention relates to a pharmaceutical composition, in particular to a pharmaceutical composition for preparing drug delivery nano/micro bubbles.

2. Description of the Prior Art

Unlike small molecule drugs that are manufactured by synthesis, biologics (i.e. macromolecular drugs such as protein drugs, polysaccharide drugs) are synthesized in vivo by bacterial or mammalian cells as a platform. Although the threshold for preparation is relatively high, many advantages of biologics are provided, such as higher compatibility with human body, higher targeting capability and lower toxicity. Therefore, biologics have gradually emerged since the past decade and become popular drugs and occupied a great market demand in the world.

However, hydrophilic macromolecule drugs such as proteins, peptides, polysaccharides and nucleic acids, due to their structural properties and instability in the gastric acid, often must be prepared as injection dosage. To improve the inconvenience brought by invasive treatment, the development of a suitable pharmaceutical carrier for the preparation of oral dosage forms has been the current trend in recent years.

Common drug carriers for oral dosage form contain nano/micro particulate carriers composed of liposome, chitosan and γ-polyglutamic acid (γ-PGA). For example, the latter chitosan and γ-PGA carrier system has good tolerance to gastric acid and can be dissolved in the small intestine to release the active ingredient encapsulated therein. But its manufacturing process is very complicated, i.e. a precursor drug must be mixed and dried with special manufacturing process, and then coated in gelatin capsules. This will cause difficulties for practical mass production. Furthermore, capsule dissolution in the small intestine is often incomplete and difficult to be controlled resulted in likely affected efficacy. Therefore, there is a need to provide better dosage forms for patients with needs in long-term application of those drugs.

In summary, it is a current goal in related industries to develop suitable oral dosage forms for macromolecule drugs.

SUMMARY OF THE INVENTION

In view of the problems of the conventional arts described above, one objective of the present invention is to provide a pharmaceutical composition for preparing drug delivery nano/mirco bubbles, which can be effectively used for drug delivery, release and absorption in humans.

For purposes of this invention, a pharmaceutical composition includes a drug layer comprising an active ingredient, a surfactant, an acidic component and an effervescent ingredient. The active ingredient comprises a nucleic acid, a peptide or a protein. The acidic component and effervescent ingredient of the drug layer are dissolved in the water to react for generating carbon dioxide and bubbles thereof. The surfactants surround the carbon dioxide gas core and form a double-layer structure having an inner layer and outer layer. The active ingredient is embedded in a gap formed between the inner layer and the outer layer of the double-layer structure.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIGS. 2 to 5a and 5b are experimental data of an embodiment of the present invention;

FIG. 6b is a partial enlarged view of FIG. 6a.

DESCRIPTION OF THE PREFERRED EMBODIMENT

The invention will be further detailed by following preferred embodiments with accompanied drawings. It is noted that the experimental data disclosed in the following embodiment are used for illustrating the technical features of the present application and not intended to limit the aspects which may be implemented.

Figure 1:
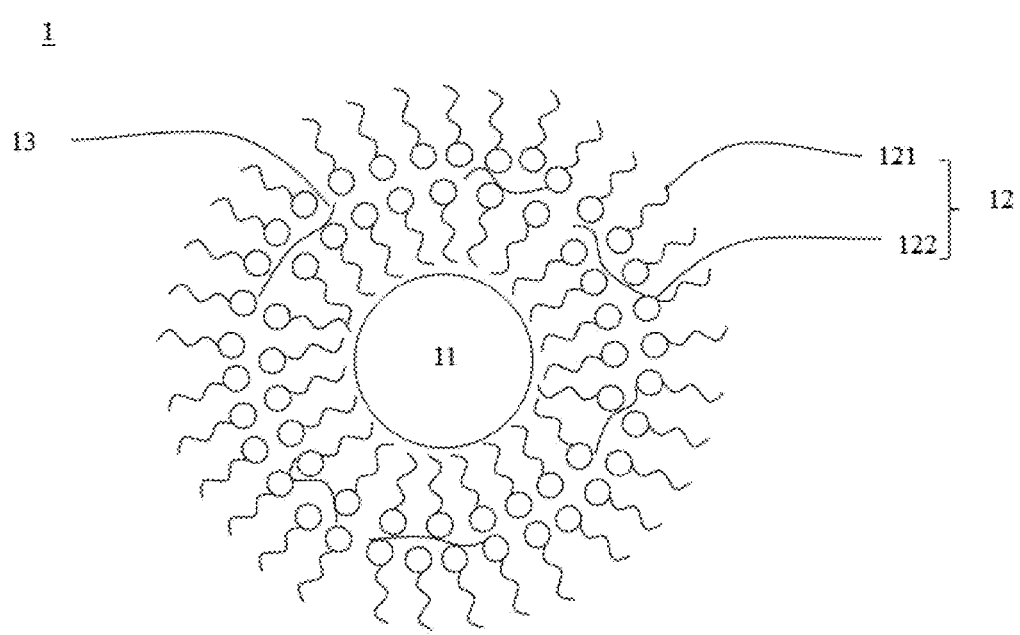
FIG. 1 is a schematic diagram illustrating the nano/micro bubbles according to one embodiment of the present invention.

Refer to FIG. 1, which is a schematic diagram illustrating the nano/micro bubbles 1 according to one embodiment of the present invention, wherein surfactants 12 surround the gas core 11 and form a double-layer structure. Each surfactant 12 has a hydrophilic head 122 and a hydrophobic tail 121 and the double-layer structure is comprised with an inner layer and an outer layer formed by the surfactants 12. The surfactants 12 in the inner layer face the gas core 11 with their hydrophobic tails 121 and the surfactants 12 in the outer layer face towards the outer side of the nano/mirco bubble 1 with their hydrophobic tails 121. The surfactants 12 in the inner layer and the surfactants 12 in the outer layer of the double-layer structure align to each other with their hydrophilic heads 122 to form the double-layer structure. The active ingredient 13 is embedded in a gap formed between the inner layer and the outer layer of the double-layer structure. Wherein, the gas core 11 of carbon dioxide, air or other gases may be encapsulated by the surfactant 12.

The particle diameter of the nano/micro bubbles of the present invention mainly depends on the size of the gas core and thus may vary in large ranges. In one embodiment, the particle diameter of nano/micro bubbles may mainly range between 50 nm-100 μm.

It should be noted that the existence of the gas core 11 in the nano/micro bubbles of the present invention is quite important while the center of conventional liposomes or cell membranes is filled with liquid. Therefore, the nano/micro bubbles of the present invention may be distinguished from conventional liposomes or cell membranes.

Furthermore, it should be noted that, in one preferred embodiment, the double layer structure of the nano/micro bubbles formed by the surfactant 12 may be in the opposite way from the lipid bilayer provided in conventional liposomes or cell membrane. To be specific, the hydrophobic tails 121 of the surfactant 12 face the gas core 11 and towards the outer side of the nano/micro bubbles 1 and the hydrophilic heads 122 are arranged opposite to each other to form the double-layer structure so as to maintain hydrophobicity against water. However, the hydrophilic heads of the conventional lipid bilayers structure face the center and towards the outer side, and arranged opposite to each other with hydrophobic tails to form a bilayer structure.

In general, surfactant 12 can be classified as anionic surfactants, cationic surfactants, amphoteric or non-ionic surfactants. Anionic surfactants may include, but are not limited to, alkyl sulfates, sodium dodecyl sulfate, n-dodecyl benzene sulfonate, sodium laureth sulfate and so on. The cationic surfactants may include, but are not limited to, polyoxyethylene lauryl dimethylamine salts and so on. The nonionic surfactant may include, but are not limited to polyoxyethylene sorbitan monostearate and so on.

As shown in FIG. 1, active ingredient 13 may be embedded in the gap formed between hydrophilic heads of surfactant arranged opposite to each other; therefore, the size of the active ingredient 13 is not particularly limited. The active ingredient 13 may be small molecular drug or biological macromolecules. In a preferred embodiment, the active ingredient 13 may comprise nucleic acid, peptide or protein. Here, the nucleic acid comprises deoxyribose nucleic acid (DNA) or ribose nucleic acid (RNA). Proteins as the active ingredient of the present invention may include enzymes, cytokines, growth factors, hormones, vaccines, antibodies and the like. More particularly, preferred proteins as the active ingredient of the present invention include gene products such as insulin, erythropoietin, somatotropin, growth hormone releasing factor, platelet derived growth factor, epidermal growth factor, transforming growth factor α, transforming growth factor β, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin and the like. Preferred overexpressed gene products are human gene products. Protein may comprise an antibody or a protein drug.

In a preferred embodiment, the active ingredient 13 may be hydrophilic so as to increase the hydrophilic interaction between the active ingredient and the hydrophilic head of the surfactant. Hydrophilic active ingredient 13 may be, but are not limited to, insulin, DNA, and so on.

In a preferred embodiment, the surfactant is chosen based on electric charge of the active ingredient 13 so as to increase the binding affinity between the active ingredient and surfactant. In the case of DNA as the active ingredient, for example, since DNA is negatively charged, some cationic surfactants that are positively charged may be chosen so as to enhance the binding affinity between the active ingredient and surfactant.

Figure 6A:
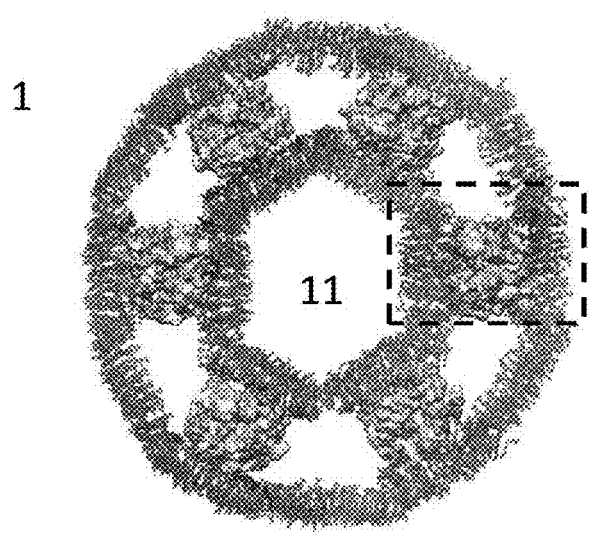
FIG. 6a is schematic diagram illustrating the nano/micro bubbles according to one embodiment of the present invention.
Figure 6B:
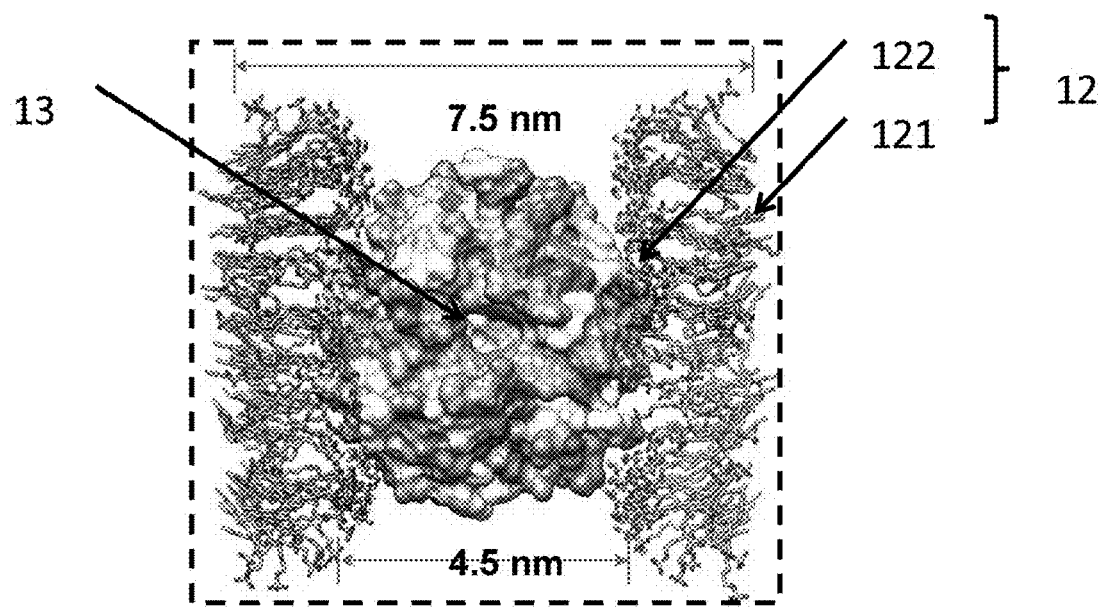

Further referring to FIGS. 6a and 6b of the present invention, which are schematic molecular simulation illustrating the nano/micro bubbles of the present invention, wherein FIG. 6b is an enlarged partial view of FIG. 6a. As shown in the example of the diagram, the gap formed between the inner layer and the outer layer of the double layer structure may be 4.5 nm, and the width of the double-layer structure may be 7.5 nm. Here, the active ingredient 13 may be an insulin and embedded in the formed gap.

The drug delivery nano/micro bubbles of the present invention may be a pharmaceutical composition prepared as tablets or capsules. The pharmaceutical composition comprises a surfactant, an effervescent ingredient and an active ingredient. The effervescent ingredient is able to react with an acid to generate carbon dioxide in a preferred embodiment. The effervescent ingredient comprises a carbonate or bicarbonate, including but not limited to, sodium bicarbonate, sodium carbonate or ammonium bicarbonate and the like. By exposing the formulations of the present invention to the acidic environment containing acids, carbon dioxide is generated by the reaction of effervescent ingredient and acid. As carbon dioxide is generated in a "burst" way, the surfactant of the formulation thus encapsulate carbon dioxide gas core to form the double-layer structure of the present invention and the active ingredient is located in the gap to obtain nano/micro bubbles of the present invention.

In a preferred embodiment, the formulation of the present invention further comprises an acidic ingredient, which may be dissociated or hydrolyzed in the water to form an acid, thereby enabling the effervescent ingredient to generate carbon dioxide in the water. In such embodiment, the formulation of the present invention can produce local acidic environment as described above and functions in a neutral or alkaline environment to obtain nano/micro bubbles of the present invention. The acidic ingredient comprises an organic acid or an inorganic acid. For example, the acidic ingredient is selected from the group consisting of tartaric acid, malic acid, maleic acid, fumaric acid, succinic acid, lactic acid, ascorbic acid, amino acid, glycolic acid, adipic acid, boric acid, potassium hydrogen tartrate and anhydrides thereof. The organic acid may include anhydrides, including but not limited to, citric anhydride, succinic anhydride, citric anhydride or other suitable organic acid anhydrides.

The ratio of the acidic ingredient, effervescent ingredient and surfactant in the formulation of the present invention may be easily modified for those skilled in the art. For example, the molar ratio of the acidic ingredient, effervescent ingredient and surfactant in one example is 5:21:6 so as to generate carbon dioxide for the reaction of the acidic ingredient and effervescent ingredient in the presence of water.

In a preferred embodiment, the formulation of the present invention further comprises an enteric coating layer encapsulating the drug layer. The enteric coating layer may be made of, but are not limited to, (methyl) acrylic acid copolymer, hydroxypropyl cellulose phthalate ester, hydroxypropyl cellulose acetate ester, hydroxypropyl cellulose acetate succinate ester or carboxymethyl ethyl cellulose.

For example, in one embodiment, the drug layer may be further filled into gelatin capsules, and the outer surface of the capsule is then coated with EUDRAGIT® by coating techniques so as to dodge damage caused by gastric acid. The ingredients of the drug layer are released until arrival at the small intestine, and the effervescent ingredient generates carbon dioxide by reacting with acidic ingredient in the water. In such embodiment, the formulation of the present invention may be utilized to produce local acidic environment in an alkaline environment (e.g., the small intestine) so that the above reaction may carry out to obtain the nano/micro bubbles of the present invention.

In terms of pharmaceutically acceptable excipients, the pharmaceutical composition may comprise optional additives, such as pharmaceutically acceptable carrier or diluents, flavorants, sweeteners, preservatives, anti-oxidants, wetting agents, buffering agents, release controlling components, dyes, adhesives, suspending agents, dispersing agents, coloring agents, disintegrating agents, excipients, film forming agents, lubricants, plasticizers, oils, or any combination of two or more of the above.

Suitable pharmaceutically acceptable carrier or diluent agents include, but not limited to, ethanol, water, glycerol, propylene glycol or glycerol, diethylene glycol monoethyl ether, vitamin A and E oils, mineral oil, PPG2 myristyl propionate, potassium phosphate or silica. Suitable lubricants include sodium oleate, sodium stearate, sodium lauryl fumarate, magnesium stearate, sodium benzoate, sodium acetate and sodium chloride. Suitable suspending agents include bentonite, ethylated isostearyl alcohols, polyoxyethylene sorbitol and sorbitan esters, microcrystalline cellulose, aluminum metahydroxide, agar and tragacanth glue, or a mixture of two or more of these substances. Suitable dispersing and suspending agents include synthetic rubbers and natural rubbers, such as vegetable gum, tragacanth, acacia, alginate, dextran, sodium carboxymethyl cellulose, methyl cellulose, polyvinyl-pyrrolidone and gelatin. Suitable film-forming agents include hydroxypropylmethylcellulose (HPMC), ethylcellulose (EC) and Polymethylmethacrylate (PMMA). Suitable plasticizers having different molecular weights (e.g. 200-8000 Da) include polyethylene glycol, polypropylene glycol and triethyl citrate. Suitable coloring agents include ferric oxide, titanium dioxide and natural and synthetic pigments. Examples of additional additives as sorbitol, talc and tristearate.

As mentioned above, in one embodiment of the present invention, the nano/micro bubbles of the present invention is generated in the intestinal tract. Once nano/micro bubbles are in contact with the epithelial cells in intestinal epidermal, the surfactant can promote paracellular pathway as well as transcellular pathway such that the active ingredient of the present invention can be delivered to deeper sites of the body circulation.

The present invention is further illustrated by the following working examples, which should not be construed as further limiting.

Preparation of Nano/Micro Bubble Formulation

The surfactant is for SDS, the acidic ingredient is for DTPA dianhydride (diethylenetriaminepentaacetic dianhydride), the effervescent ingredient is for baking soda (sodium bicarbonate, SBC), the active ingredient is for insulin, and the enteric coating layer is for EUDRAGIT® L100-55. The preparation is listed as following:
1. SDS (7 mg), DTPA dianhydride (14 mg), SBC (7 mg), insulin (5 IU/Kg) were uniformly mixed and filled into gelatin capsules.
2. The prepared gelatin capsules as described above are coated with EUDRAGIT® L100-55 (10%) and then dried.

Verification of Nano/Micro Bubbles

Figure 2:
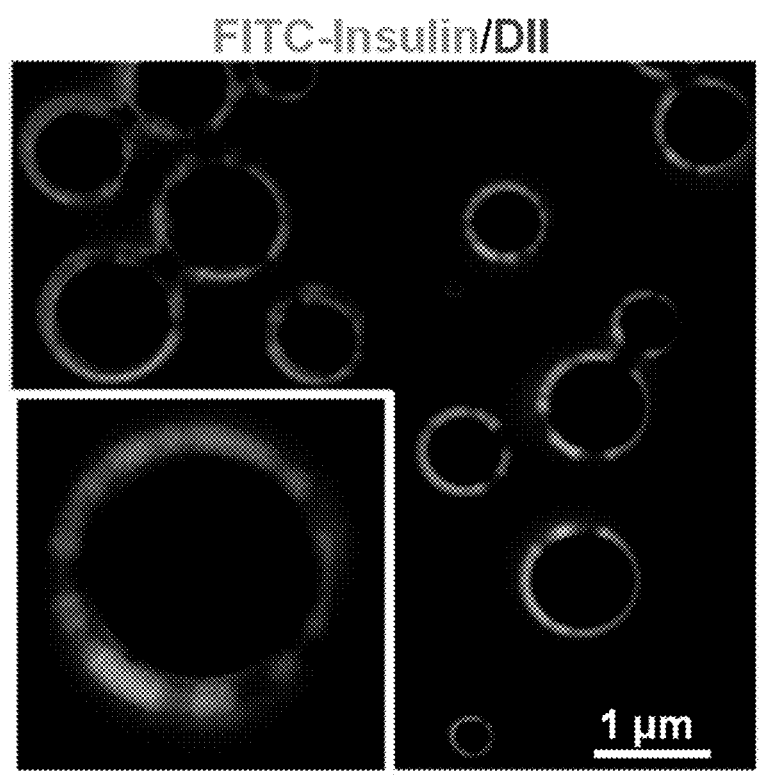

Referring to FIG. 2, the insulin was labeled with FITC, and the hydrophobic tail of SDS was stained with a fluorescent lipophilic cationic indocarbocyanine dye DII (1,1'-dioctadecyl-3,3,3',3'-tetramethylindocarbocyanine perchlorate), respectively. The obtained fluorescence images proved that insulin does exist in the nano/micro bubbles of the present invention and is located at the gap of the double-layer structure formed by the surfactant. This indicates that the active ingredient is well embedded in the nano/micro bubbles of the present invention.

Cell Images of Cells Bound with Nano/Micro Bubbles

Figure 3:
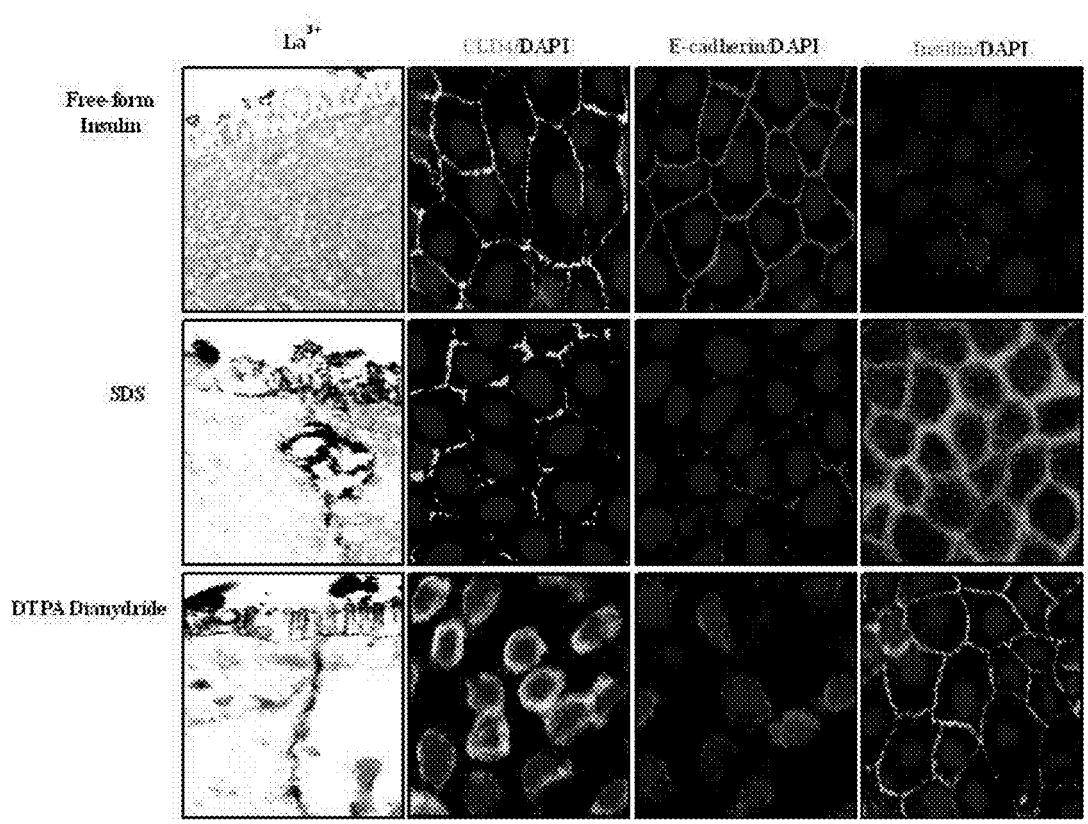

Referring to FIG. 3, which shows the images under the microscope after cells were co-cultured with the various components, wherein the cells were stained with Cld 4 (tight junction), E-cadherin (adherin junction) and DAPI (nuclear). The results showed that DTPA dianhydride can promote transmission of FITC-insulin via paracellular pathway; SDS can promote transmission of FITC-insulin via both of paracellular pathway and transcellular pathway.

In Vivo Cell Images with Nano/Micro Bubbles

Figure 4:
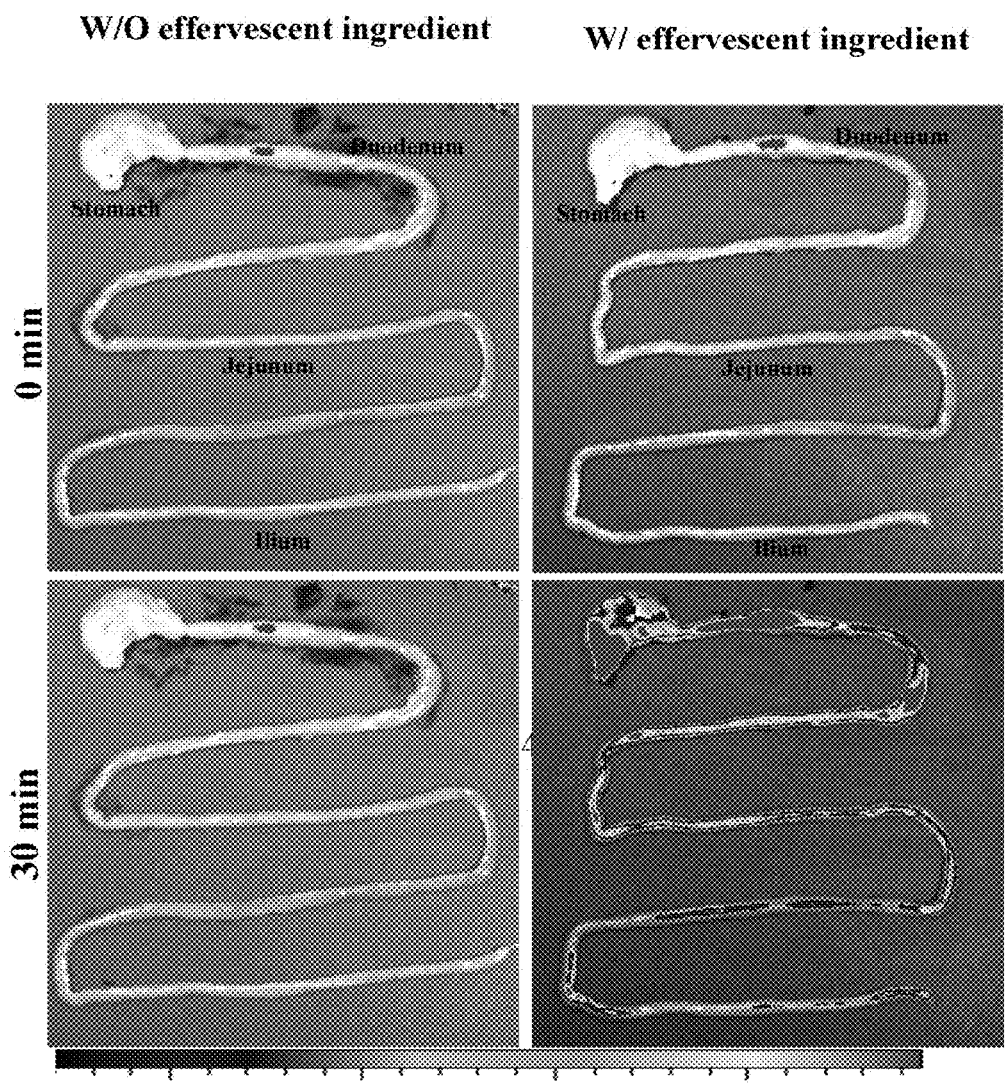

Referring to FIG. 4, which shows that the effects of nano/mirco bubbles within the intestinal tract. The distribution of the insulin can only be distributed at local area in the group without effervescent ingredient; the group with the effervescent ingredient of the present invention has demonstrated release of insulin at the middle and end section of the small intestine, in terms of nano/micro bubble burst leading to the release of insulin in the aid of the effervescent ingredient, resulted in better release performance in comparison to the group having no effervescent ingredient.

Pharmacokinetic Test of Nano/Micro Bubbles

Animal experimental procedures were performed based on the management and use of laboratory animals guidelines promulgated by the Council of Agriculture. About 300 to 350 grams of male rats (male Wistar rats) were used. The animal experiments were performed to investigate the treatment of diabetic rats using insulin-embedded carrier system by oral administration of drugs. During experiment, the rats were administrated by oral (30 IU/Kg) and subcutaneous (5 IU/Kg) administration after the rats were fixed. At different times, the animals were placed in the blood-drawing fixation frame to expose the tail, and then the tails were disinfected with iodine to prevent bacterial infection. Followed by tail incision, blood sugar of rats was observed for changes over time with the drawn blood. Meanwhile, pharmacokinetics was measured using enzyme immunoassay.

Figure 5A:
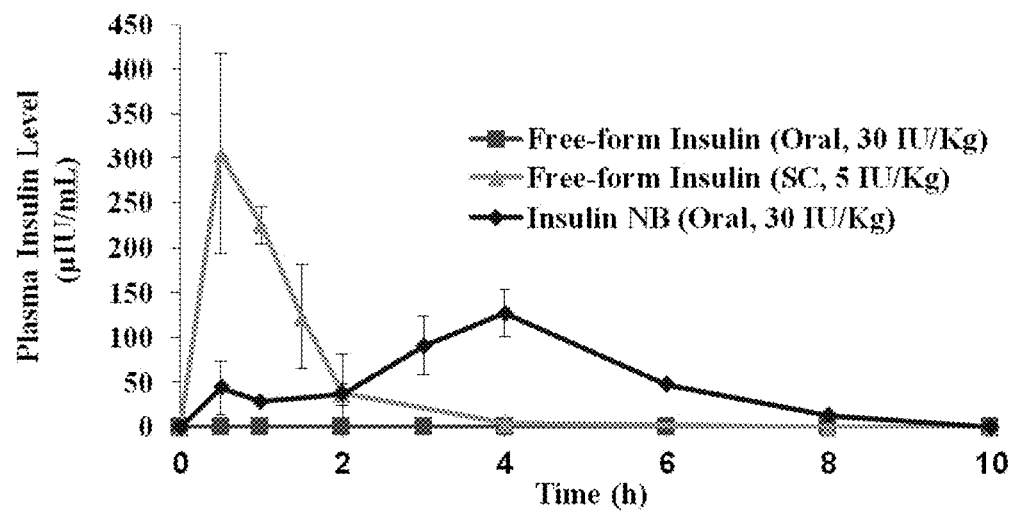
Figure 5B:
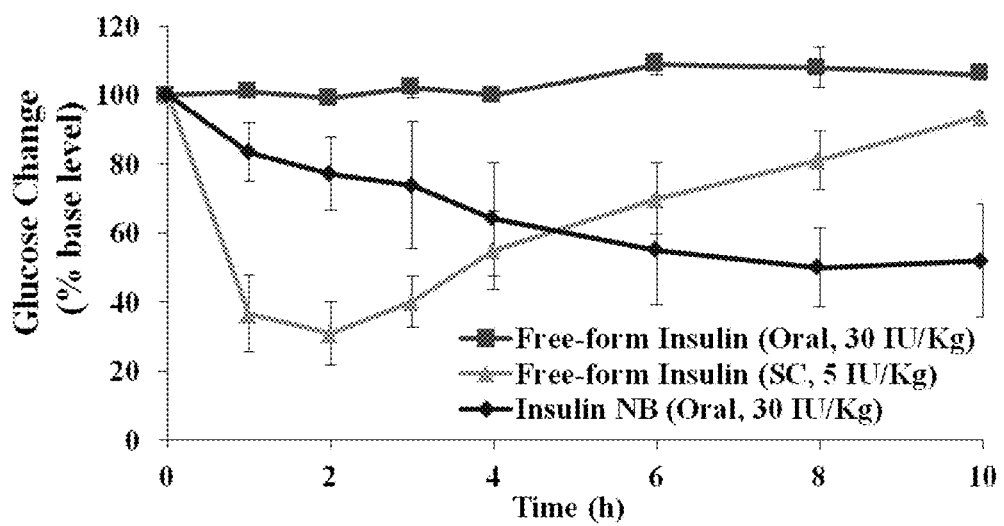

In the present example, groups comprising nano/micro bubbles of the present invention (containing 30 IU/kg of insulin), oral administration (30 IU/kg of insulin) and subcutaneous injection of insulin (5 IU/kg) are compared. The change rates in plasma insulin and blood glucose concentration from 0 to 10 hours after subjects taking insulin or injected with insulin were recorded respectively, and the results are illustrated in FIGS. 5a and 5b. Regarding change rate of the blood glucose, blood glucose rate in subcutaneous injection group rapidly declined and rose again, representing that it lacks long-term stability in controlling blood glucose levels, while the group having nano/micro bubbles then slowed down the decline of the blood glucose and maintained stability. These experiment results indicated that the nano/micro bubbles of the present invention indeed achieved sustained-release and long-lasting effects as well as good bioavailability.

In summary, the nano/micro bubbles for drug delivery of the present invention provide a novel double-layer structure having arrangement opposite to that of conventional lipid bilayers. The nano/micro bubbles burst by gas expansion generated by acid and the effervescent ingredient and interaction with intestinal epithelial cells, and then release the active ingredient in the small intestine to be absorbed by intestinal epithelial cells. The nano/micro bubbles of the present invention are provided with advantages such as being easy to prepare, having good efficiency in drug embedding and better bioavailability; therefore it can be effectively applied in development of macromolecular drug formulation.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A pharmaceutical composition for preparing drug delivery bubbles, comprising:
    a drug layer comprising:
        an active ingredient comprising a nucleic acid, a peptide or a protein,
        a surfactant,
        an acidic component and
        an effervescent ingredient, whereby the acidic component and effervescent ingredient of the drug layer are dissolved in the water to react for generating carbon dioxide and bubbles thereof, the surfactants surround the carbon dioxide gas core and form a double-layer structure having an inner layer and outer layer and the active ingredient is embedded in a gap formed between the inner layer and the outer layer of the double-layer structure.

2. The pharmaceutical composition according to claim 1, wherein the pharmaceutical composition is a tablet or a capsule.

3. The pharmaceutical composition according to claim 1, wherein the surfactant comprises an anionic surfactant, a cationic surfactant, an amphoteric surfactant or a non-ionic surfactant.

4. The pharmaceutical composition according to claim 1, wherein the surfactants comprise sodium dodecyl sulfate, polyoxyethylene sorbitan monostearate, sodium laureth sulfate or sodium dodecyl benzene sulfonate.

5. The pharmaceutical composition according to claim 1, wherein the effervescent ingredient comprises a carbonate or a bicarbonate.

6. The pharmaceutical composition according to claim 1, wherein the acidic ingredient comprises an organic acid or an inorganic acid.

7. The pharmaceutical composition according to claim 1, wherein the acidic ingredient comprises diethylenetriaminepentaacetic dianhydride (DTPA anhydride).

8. The pharmaceutical composition according to claim 1, wherein the active ingredient comprises insulin, erythropoietin, somatotropin, platelet derived growth factor, epidermal growth factor, transforming growth factor α, transforming growth factor β, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, granulocyte-macrophage stimulating factor or macrophage colony stimulating factor.

9. The pharmaceutical composition according to claim 1, further comprising a gelatin layer, wherein the drug layer is coated with the gelatin layer.

10. The pharmaceutical composition according to claim 1, further comprising an enteric layer, wherein the drug layer is coated with the enteric layer.

11. The pharmaceutical composition according to claim 10, wherein the enteric coating layer comprises (methyl) acrylic acid copolymer, hydroxypropyl cellulose phthalate ester, hydroxypropyl cellulose acetate ester, hydroxypropyl cellulose acetate succinate ester or carboxymethyl ethyl cellulose.

12. The pharmaceutical composition according to claim 1, wherein the drug layer further comprises a release controlling component.

13. The pharmaceutical composition according to claim 1, wherein the pharmaceutical composition is an oral pharmaceutical composition.

14. The pharmaceutical composition according to claim 1, wherein the active ingredient is an insulin.

* * * * *